United States Patent [19]

Laddach et al.

[11] 4,241,767
[45] Dec. 30, 1980

[54] METHOD AND DEVICE FOR FEEDING WEFT WIRES

[75] Inventors: Hans Laddach; Werner Oertel, both of Dusseldorf, Fed. Rep. of Germany

[73] Assignee: Hein, Lehmann Aktiengesellschaft, Dusseldorf, Fed. Rep. of Germany

[21] Appl. No.: 23,579

[22] Filed: Mar. 26, 1979

Related U.S. Application Data

[63] Continuation-in-part of Ser. No. 859,430, Dec. 12, 1977, abandoned.

[30] Foreign Application Priority Data

Dec. 11, 1976 [DE] Fed. Rep. of Germany ....... 2656188

[51] Int. Cl.³ .............................................. D03D 47/12
[52] U.S. Cl. ..................................... 139/443; 139/429
[58] Field of Search ................ 139/429, 443, 452, 142

[56] References Cited

U.S. PATENT DOCUMENTS

| 2,401,070 | 5/1946 | Harter | 139/443 |
| 3,081,798 | 3/1963 | Stauffer et al. | 139/443 |
| 3,095,910 | 7/1963 | Deady et al. | 139/443 |
| 3,160,178 | 12/1964 | Meckley | 139/443 |
| 3,799,212 | 3/1974 | Stanislav et al. | 139/452 |

*Primary Examiner*—Henry Jaudon
*Attorney, Agent, or Firm*—Allison C. Collard; Thomas M. Galgano

[57] ABSTRACT

A fill wire feeder for feeding weft wire to a wrap shed from a lay beam includes a weft wire feeding mechanism disposed outside of the wrap shed and mounted on one end of the lay beam. The mechanism includes two pairs of coacting rotatable rollers, the nips between each pair of which lie in the same plane to define a linear travel path for the weft wire guided therebetween and drive means for rotating at least one roller of each of the pairs.

5 Claims, 5 Drawing Figures

METHOD AND DEVICE FOR FEEDING WEFT WIRES

This application is a continuation-in-part of application Ser. No. 859,430, filed Dec. 12, 1977 now abandoned.

The present invention relates to a method and a device for making wire webs consisting of weft wire and warp wire. More particularly, it relates to a fill wire feeder for a wire loom, wherein weft wire is mechanically introduced into a weaving-feed device, and is subsequently cut and is admitted by a weaving batten.

Such methods are used, for example, for making wire webs or screens for the sieve and conveying technique. Thereby, the wire webs or screens may be made from metal and/or plastic material.

In a known method of this type, the weft wires are introduced into the weaving feed device by means of a so-called plug-arm device. For this purpose, the plug-arm device is provided with two arms which simultaneously engage the weave feeding device. Thereby, the weft wire is first drawn into the weave-feeding device by one arm to the half of its weft-wire length, and it is then gripped by the second arm and is completely drawn through the weave feeding or loading device. The arms are usually mechanically driven by means of a very expensive kinematic mechanism. However, plug-arm devices require a lot of space, are heavy, are subject to breakdowns, and are expensive to make. The mass forces generated by the device result in a deflection of the weft wires and a damaging of the weave feeding means, as a result of which the weft wires are disadvantageously woven into the web in a bent condition. In plug-arm devices, the length of the arms also predetermines the width of the wire web which is a limiting factor.

It is, therefore, an object of the invention to provide a method and a device for making wire webs which is inexpensive and can be carried out in a simple manner and such that wire webs can be made of the highest quality as well as with different dimensions.

This object of the invention is achieved in that the weft wire is pushed into the weaving feed device. For this purpose, it is advantageous that the weft wires have a certain inherited stability in accordance with the suitable length; that is, the weft wire does not bend under its own weight. The sliding into the weave-loading device may be carried out in a simple manner either electrically, mechanically or pneumatically. Thereby, no special preparation tools are required which have to be introduced into the weave feeding means and which would have to be removed therefrom. In this manner, wire webs having different measurements, in particular, different wire widths and mesh widths, may be made.

The substantially interference-free and safe introduction of the weft wire is made possible if one end of the weft wire is bent upwardly before introducing the same into the weft feed means. Hence, each weft is provided with a guiding end which slides through the web feeding means above the lower warp wires during the introduction without threading.

The bending upwardly of the weft wire can be carried out at the same time when cutting the desired length of the wires. A particularly effective and safely operating device for carrying out the inventive method is provided when the weft wire introduction is provided completely outside of the wrap shed at the weft-loading device, and in that a feeding mechanism is provided for the weft wire with at least two associated rollers which run in one plane, whereby at least one of the rollers is coupled with a drive.

Other objects and features of the present invention will become apparent from the following detailed description when taken in connection with the accompanying drawings which disclose a single embodiment of the invention. It is to be understood that the drawing is designed for the purpose of illustration only, and is not intended as a definition of the limits and scope of the invention disclosed.

In the drawings, wherein similar reference numerals denote similar elements throughout the several views.

Figure 1:
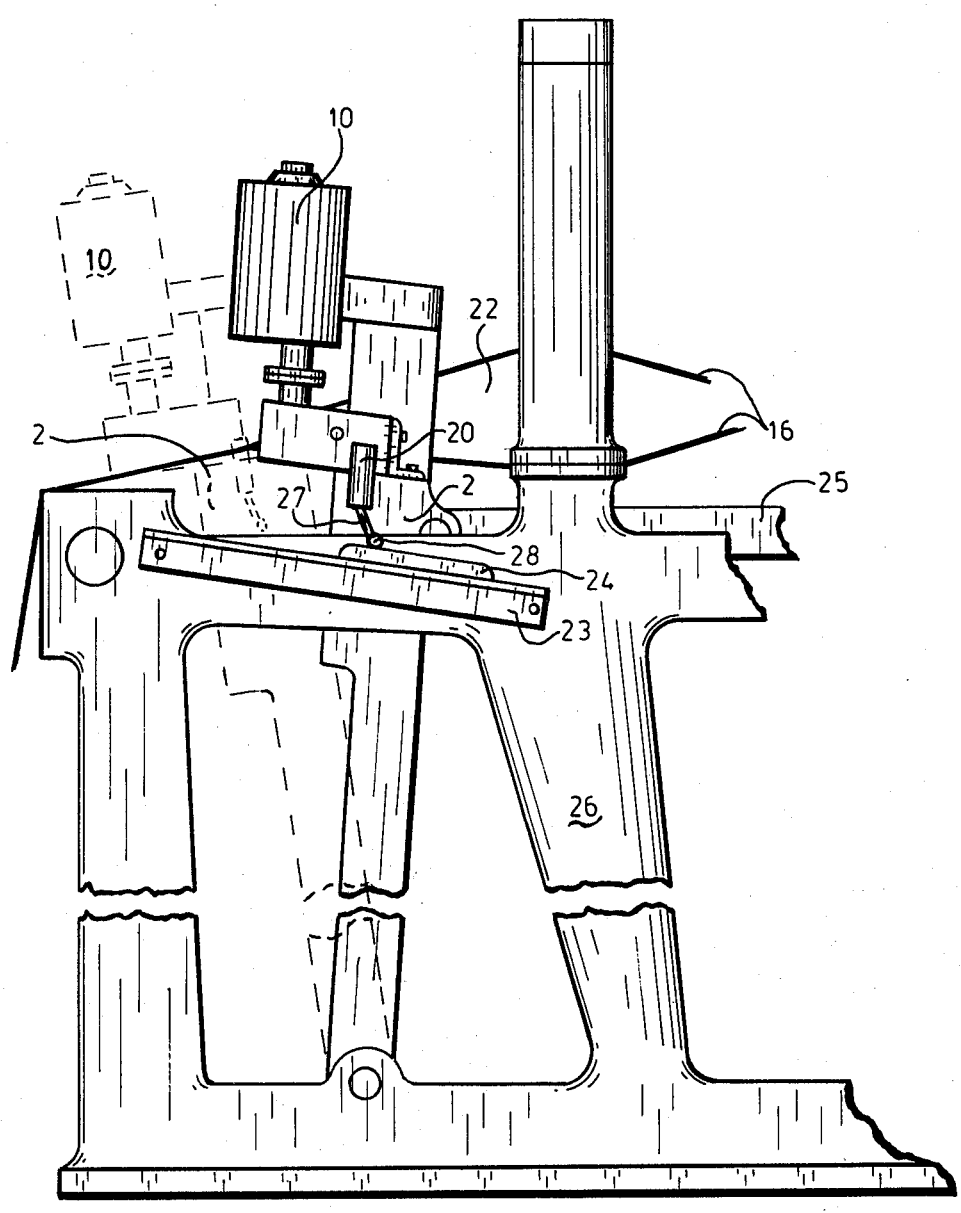
FIG. 1 is a side elevational view of the front portion of a wire weaving machine for making wire mesh or wire lattice from warp and weft wires embodying the present invention.

Referring now in detail to the drawings, FIG. 1 is a side view of the front portion of a wire weaving machine for making wire mesh or wire lattice from warp and weft wires. The wire weaving machine has a frame 26. A lay beam 2 is pivotably mounted in frame 26. At one end of lay beam 2, a limit switch 20 is mounted. Limit switch 20 is provided with a pivotable finger 27, at the end of which a roller 28 is mounted. The limit switch opens and closes the circuit for supplying current to motor 10. A rail 23 is associated with the limit switch and an adjustable cam-like border 24 is mounted on rail 23. Rail 23 is retained on frame 26 in an almost horizontal position. Limit switch 20 and rail 24 are so positioned that the rail 24 engages the limit switch during a substantial portion of the forward and rearward movement of lay beam 2, which, for example, is driven by means of rods 25 and an eccentric drive. Only shortly before and shortly after engagement of the lay beam 2 does rail 24 release finger 27 of limit switch 20 and switch-off the same. During the switching-on phase of limit switch 20, weft wire 3 is fed into the wrap shed 22. The position of lay beam 2 in its engagement point is shown in dash-dot lines in FIG. 1.

Figure 2:
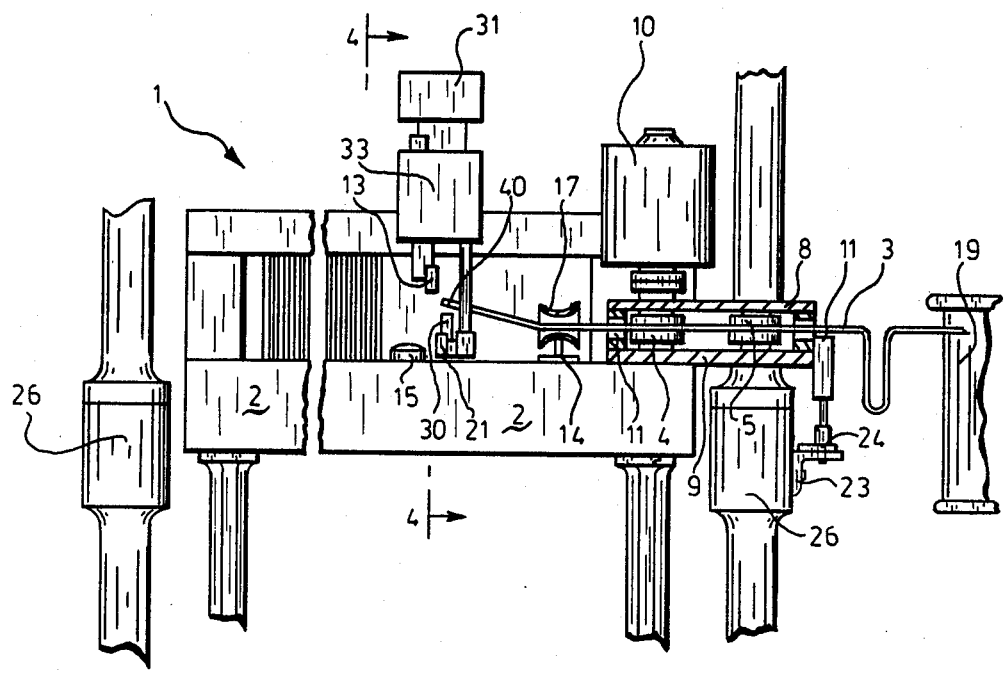
FIG. 2 is a plan view, of the weaving machine shown in FIG. 1, and showing, in section, a fill wire feeder.

FIG. 2 shows a sectional view of the inventive fill wire feeder 1. It is mounted on one end of the lay beam 2. The opposite end of the lay beam 2 remains free or unencumbered. Fill wire feeder 1 is arranged completely outside of wrap shed 22. In no phase of the operation does a part of fill wire feeder 1 extend into wrap shed 22. Fill wire feeder 1 is provided with a weft wire feeding mechanism for the weft wire 3. In the present case, the feeding mechanism consists of four rollers 4, 5, 6, and 7, which are arranged in pairs with respect to each other. In particular, when working with comparatively soft wires, for example, Siemens-Martin-steel, one pair of rollers 4, 6 is sufficient for feeding the weft wires. Rollers 4, 5, 6 and 7 are disposed between a cover plate 8 and a bottom plate 9. Only roller 4 which belongs to the pair of rollers adjacent to the wrap shed 22 is provided with a drive 10 having an electric motor.

The electric motor can be switched off and on by limit switch 20. The "switching on" time defines the length of the introduced or fed weft wire. Fill wire feeder 1 is provided with an input and output guiding slot 11 for the weft wire 3. In addition, a guide 12 may be provided at the input side in the form of a funnel-shaped pipe.

Coupled with lay beam 2, is a cross cutting device for the weft wire which is disposed behind the fill wire feeder. This cross cutting device is provided with two counter-running coacting knives 13, 21 and a weft wire guiding piece 14. The intersecting point of knives 13, 21 is so chosen that it is located above the opening cross section 17 of the weft wire guiding piece 14. Thereby, the weft wire is automatically bent upwardly during cross cutting and is thereby provided with a guide shoe or upwardly bent guiding end 40. The drive 31 of knives 13, 21 may be done hydraulically, pneumatically, mechanically or electrically.

A feeding guide 15 facilitates the feeding of the weft wire into the wrap shed. The weft wire which is usually pre-shaped or pre-bent is rolled off a reel 19 in accordance with the inventive method over a stepless adjustable bending machine (not shown) and past roller 4 of the fill wire feeder 1; the input guiding slots 11 as well as the nips formed between rollers 4, 6 and 5, 7 being in alignment. When the limit switch 20 activates a corresponding pulse after being actuated by rail 24, electric motor 10 is switched on. When the electric motor 10 is switched on the weft wire 3 is fed into the wrap shed 22 for this time period. The guide shoe 40 which is shaped by the bending is able to slide over the lower warp wires without threading or hooking since it, in effect, acts like the tip of a ski. Before the weft wire reaches the wrap shed it passes the cross-cut cutting device and thereafter the feeding guide 15. When the weft wire has reached its required length the limit switch which is coupled with the movement mechanism of the lay beam can switch off the electric motor. During the engagement position of the lay beam 2, (the position shown in phantom line in FIG. 1), knives 13, 21 cut off the weft wire 3 and simultaneously bend it. After the engagement of the weft wire a new operating cycle starts. The time period of one operating cycle may be kept comparatively low, so that a high weaving speed may be obtained. This is also possible because the cutting of the weft wire may be done during the engagement. The weight of the inventive weft wire feeding is so low that only very low mass forces act upon the lay beam. Thereby, a very even wire mesh may be produced having straight weft wires.

Figure 3:
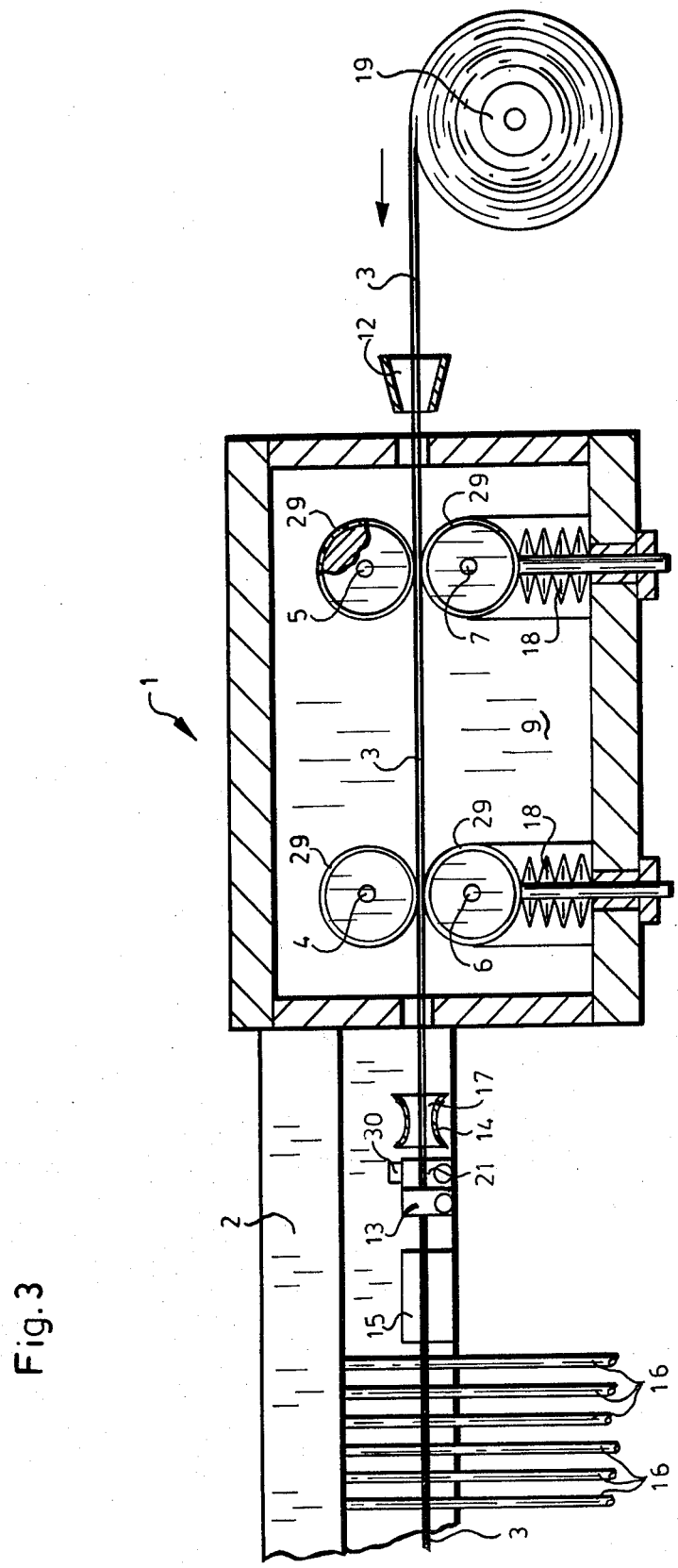
FIG. 3 is a horizontal sectional view of the fill wire feeder shown in FIG. 2.

FIG. 3 is a plan view of the inventive fill wire feeder 1 in cross section. There are four rollers 4, 5, 6, and 7, each of which is coated with plastic (preferably polyurethane) and has a cylindrical running face 29. The plastic has a high degree of abrasion resistance and keeps any slipping between the weft wire and running face to a minimum. Only roller 4 is moved by drive 10. This roller 4 generates the feeding movement of weft wire 3. Rollers 4 and 5 can only execute rotating movements. Otherwise they are rigidly mounted or fixed in position. Rollers 6 and 7 which are associated with rollers 4, 5 are mounted in roller bearings for easy motion. Rollers 6 and 7 are constantly movable and are biased against rigidly mounted rollers 4, 5 by means of spring pressure. The required spring pressure is generated by a number of cup springs 18 which are in the form of a pack. The spring pressure of the cup springs 18 can be adjusted in stepless fashion.

Figure 4:
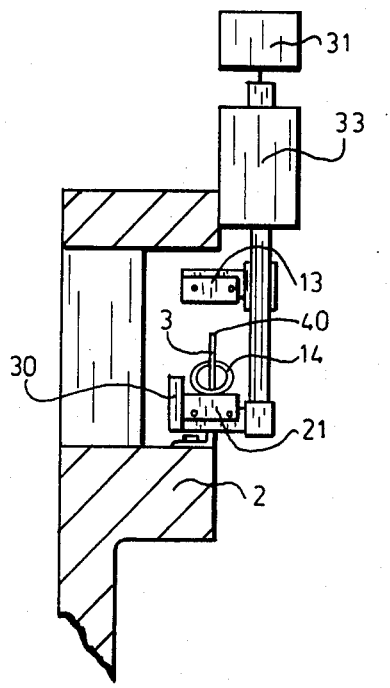
FIG. 4 is a sectional view taken along lines IV—IV of FIG. 2, showing the cutting knives in a non-operative rest position.

FIG. 4 is a sectional view along lines IV-IV of FIG. 2, whereby knives 13, 21 of the cross cutting device are opened, that is, in the phase shortly before feeding of the weft wire into the lay beam. The lower knife is disposed below the cross section opening of the weft guide piece 14. A bordering finger 30 is mounted on the front face of lower knife 21 so as to prevent the weft wire 3 from sliding off the cutting blade of the lower knife 21. Knives 13, 21 are so mounted in a vertical neck-journal bearing 33 that they are movable in parallel manner with respect to each other and are normally disposed with respect to the lay beam 2. When the weft wire 3 is to be cut off or bent upwardly, which is carried out during the engagement of the lay beam 2, the lower knife 21 lifts the weft wire 3 and bends the wire to the point of intersection 32 of knifes 13, 21 and then cuts the wire. Thereby, the weft wire 3 is first bent upwardly and is then cut off. The drive 31 for the counter moving and parallel moving knives 13, 21 can be operated electrically, for example, electromagnetically or by means of a servo motor, pneumatically, hydraulically, or mechanically, for example, by means of a rod system which is mounted on frame 26 of the wire weaving machine and which automatically moves the knives upwardly or downwardly when the lay beam 2 engages.

Figure 5:
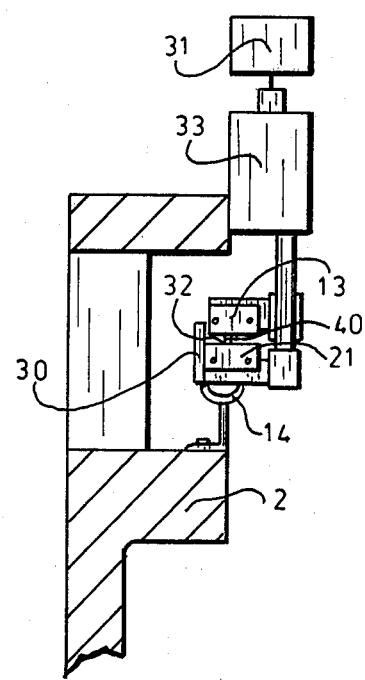
FIG. 5 is a sectional view similar to that of FIG. 4, but showing the cutting mechanism in a cutting position.

FIG. 5 shows the same view of the cross cutting device as shown in FIG. 4, however, at a point when the knives 13 and 21 cut off the weft wire and simultaneously bend the weft wire upwardly. The cutting is done simultaneously with the engagement of the lay beam.

In accordance with the inventive method, weft wires having a thickness of up to 2.5 mm and more may be used. Furthermore, difficult meshes, for example, having a mesh width of 3.0 mm and a wire cross section of 1.8 mm, or a mesh width of 2.0 mm and a wire cross section of 1.4 mm can be made. The width of the wire mesh is merely limited by the size of the wire loom. On a wire loom with a weave width of 3,000 mm it is possible to make wire meshes having a width of between almost 0 to 3,000 mm with the inventive fill wire feeder.

Thus, while only one embodiment of the present invention has been shown and described, it will be obvious to those persons of ordinary skill in the art that many changes and modifications may be made thereunto without departing from the spirit and scope of the invention.

What is claimed is:

1. A fill wire feeder mountable on one end of a movable lay beam, comprising:

a weft wire feeding mechanism including at least one pair of cooperating, force-adjustable generally cylindrical rollers, the axes of which lie in one plane, said rollers being mounted so as to be in constant communication with weft wire fed therebetween and at least one of said rollers being mounted in a fixed position, said feeding mechanism also including drive means including an electric motor coupled to said at least one roller for intermittently driving the same; and a cutting device including a weft wire tubular guiding piece for receiving weft wire from said feeding mechanism and two counter-moving and coacting knives, said knives being mounted for movement on said lay beam in a direction parallel to each other and perpendicular to said lay beam and drive means for moving said knives during the engagement of the lay beam so as to cut weft wire moved therebetween by said feeding mechanism, said counter-moving knives of said cutting device have a point of intersection which is located above the opening cross-section of said guiding piece so that simultaneously with the cutting operation one end of the weft wire is bent.

2. The feeder according to claim 1, additionally including a device for turning on and off said electric motor, said device including at least one limit switch and a rail with which it is associated, said limit switch being mounted for movement with said lay beam and said rail being mountable on a stationary frame of a device for making wire mesh, said rail being disposed in a substantially horizontal position and having an adjustable cam-like border disposed for cooperative engagement with said limit switch.

3. The feeder according to claim 1, wherein said rollers are cylindrically shaped and are provided with a plastic running sheath along the circumferential edge thereof.

4. The feed according to claim 1, wherein the other roller of said at least one pair is spring-loaded so that it is in biased engagement with the associated fixed roller.

5. The feeder according to claim 4, wherein said spring-loading of said roller is provided by means of an adjustable cup spring.

* * * * *